US012678399B2

(12) United States Patent
Rezai et al.

(10) Patent No.: US 12,678,399 B2
(45) Date of Patent: Jul. 14, 2026

(54) METHODS OF IMPROVING AUTONOMIC IMBALANCE OR SYMPATHETIC IMPAIRMENT BY REGULATING THE STELLATE GANGLION

(71) Applicant: West Virginia University Board of Governors on behalf of West Virginia University, Morgantown, WV (US)

(72) Inventors: Ali R. Rezai, Morgantown, WV (US); Milind Deogaonkar, Morgantown, WV (US); Clay B. Marsh, Morgantown, WV (US); Victor Finomore, Morgantown, WV (US)

(73) Assignee: WEST VIRGINIA UNIVERSITY BOARD OF GOVERNORS ON BEHALF OF WEST VIRGINIA UNIVERSITY, Morgantown, WV (US)

( * ) Notice: Subject to any disclaimer, the term of this patent is extended or adjusted under 35 U.S.C. 154(b) by 1377 days.

(21) Appl. No.: 17/313,152

(22) Filed: May 6, 2021

(65) Prior Publication Data

US 2021/0346625 A1     Nov. 11, 2021

Related U.S. Application Data

(60) Provisional application No. 63/021,354, filed on May 7, 2020.

(51) Int. Cl.
| | |
|---|---|
| *A61K 9/00* | (2006.01) |
| *A61B 18/14* | (2006.01) |
| *A61B 90/00* | (2016.01) |
| *A61K 31/167* | (2006.01) |
| *A61K 31/445* | (2006.01) |
| *A61K 31/573* | (2006.01) |
| *A61N 1/05* | (2006.01) |
| *A61N 5/06* | (2006.01) |
| *A61N 5/073* | (2006.01) |
| *A61N 7/00* | (2006.01) |
| *A61N 7/02* | (2006.01) |
| *A61P 11/00* | (2006.01) |

(52) U.S. Cl.
CPC ............ *A61K 9/0019* (2013.01); *A61B 90/37* (2016.02); *A61K 31/167* (2013.01); *A61K 31/445* (2013.01); *A61K 31/573* (2013.01); *A61N 5/0622* (2013.01); *A61N 7/02* (2013.01); *A61N 7/022* (2013.01); *A61P 11/00* (2018.01); *A61B 18/14* (2013.01); *A61B 2090/378* (2016.02); *A61N 1/05* (2013.01); *A61N 2005/0612* (2013.01); *A61N 2005/0626* (2013.01); *A61N 2005/073* (2013.01); *A61N*

*7/00* (2013.01); *A61N 2007/0021* (2013.01); *A61N 2007/003* (2013.01); *A61N 2007/025* (2013.01)

(58) Field of Classification Search
CPC .............. A61K 2300/00; A61K 31/167; A61K 31/445; A61K 31/573; A61K 9/0019; A61P 11/00; A61B 18/14; A61B 2090/378; A61B 90/37
See application file for complete search history.

(56) References Cited

U.S. PATENT DOCUMENTS

| | | | | |
|---|---|---|---|---|
| 6,861,449 B2 * | 3/2005 | Gleich | ............... | A61K 31/4453 |
| | | | | 514/535 |
| 8,755,890 B2 | 6/2014 | Rezai | | |
| 10,201,706 B2 * | 2/2019 | Schwab | ............... | A61N 1/3606 |
| 2006/0134008 A1 * | 6/2006 | Deaver | .............. | A61K 31/4745 |
| | | | | 424/46 |
| 2012/0270876 A1 * | 10/2012 | Yun | .......................... | A61P 37/06 |
| | | | | 514/415 |
| 2021/0205501 A1 * | 7/2021 | Bright | ................ | A61B 18/1492 |

FOREIGN PATENT DOCUMENTS

| | | | | | |
|---|---|---|---|---|---|
| WO | WO-2017007957 A1 * | 1/2017 | ........... | A61K 31/765 |

OTHER PUBLICATIONS

Totura et al. (Expert Opinion on Drug Discovery, 2019, vol. 14, No. 4, 397-412). (Year: 2019).*
Nishina et al. (Anesthesiology, 1998, 88,1300-9). (Year: 1998).*
Kiyonari et al. (Critical Care Medicine 28(2): p. 484-489, Feb. 2000) (Year: 2000).*
Chen et al. (Inflammation, 41, Oct. 5, 2018) (Year: 2018).*
Kaye et al. (Best Practice & Research Clinical Anesthesiology, 33, 3029, 465-486) (Year: 2019).*
Piracchini, p. 3, Equipment, https://www.ncbi.nlm.nih.gov/books/NBK507798/2023 (Year: 2023).*
Hirakawa (Nerve Blockade and Interventional Therapy, Ed. Ohseto et al. 2019, p. 83-90, Chapter 22, Stellate Ganglion Block) (Year: 2019).*
NHLBI, https://www.nhlbi.nih.gov/ health/ards/treatment, 2025 (Year: 2025).*
Mayo Clinic, https://www.mayoclinic.org/ diseases-conditions/ards/diagnosis-treatment/drc-20355581, 2025 (Year: 2025).*
Shima, Acute Medicine & Surgery 2022 (Year: 2022).*
Mapp, Title and Abstract, Eur Respir J 2000; 16: 570-572 (Year: 2000).*

* cited by examiner

*Primary Examiner* — Umamaheswari Ramachandran
(74) *Attorney, Agent, or Firm* — Tarolli, Sundheim, Covell & Tummino LLP

(57) ABSTRACT

Methods of improving ARDS by regulating a stellate ganglion is provided herein. Methods of improving a hypercoagulation state are also provided by regulating the sympathetic nervous system.

19 Claims, 1 Drawing Sheet

METHODS OF IMPROVING AUTONOMIC IMBALANCE OR SYMPATHETIC IMPAIRMENT BY REGULATING THE STELLATE GANGLION

CROSS-REFERENCE TO RELATED APPLICATIONS

The present application claims priority to U.S. Provisional No. 63/021,354 filed on May 7, 2020, which is incorporated by reference in its entirety.

TECHNICAL FIELD

The present disclosure relates to methods of improving autonomic nervous system imbalance and/or sympathetic impairment by modulating or otherwise regulating the stellate ganglion.

BACKGROUND

Coronavirus Disease 2019 (COVID-19) (also known as "SARS-CoV-2") is currently a pandemic with a high incidence of Acute Respiratory Distress Syndrome (ARDS). ARDS is pulmonary edema of non-cardiac origin that can be due to acute lung injury, anaphylactic reactions, or anaphylatoid reactions, for example, resulting in respiratory compromise and high mortality. Currently, there are no definite treatment for ARDS in COVID-19 with a mortality of 50% in severe cases. The current treatment strategy is focused towards reducing potential exposure and improving the patient's clinical status with the best available medical management. The efforts at prevention of the spread by exposure has led to massive lockdown in many parts of the USA and worldwide resulting in economic crisis. At the same time, there is a lack of any specific treatment. The fulminant course of disease secondary to COVID-19 induced ARDS, has led to a higher incidence of mortality and an unprecedented health care crisis. Even for survivors, there is often a prolonged stay in the intensive care unit (ICU), which further limits ICU bed and ventilator availability resulting in overburdened health care facilities and a scarcity of valuable life-saving resources. Continued COVID-19 outbreaks and increasing healthcare burden is expected to overwhelm existing health care resources, especially ICU and ventilator availability, unless the "infection spread curve" is flattened. Even with that, the current rate of ARDS, associated mortality, and prolonged ICU stay from COVID-19 is very high.

SUMMARY

Methods, systems and devices are provided herein to improve autonomic nervous system (ANS) imbalance and/or sympathetic impairment mediated by the stellate ganglion or other components of the ANS (the sympathetic nervous system (SNS) and/or parasympathetic nervous system (PNS)) in a patient in need thereof.

DETAILED DESCRIPTION

Figures 1, 2:
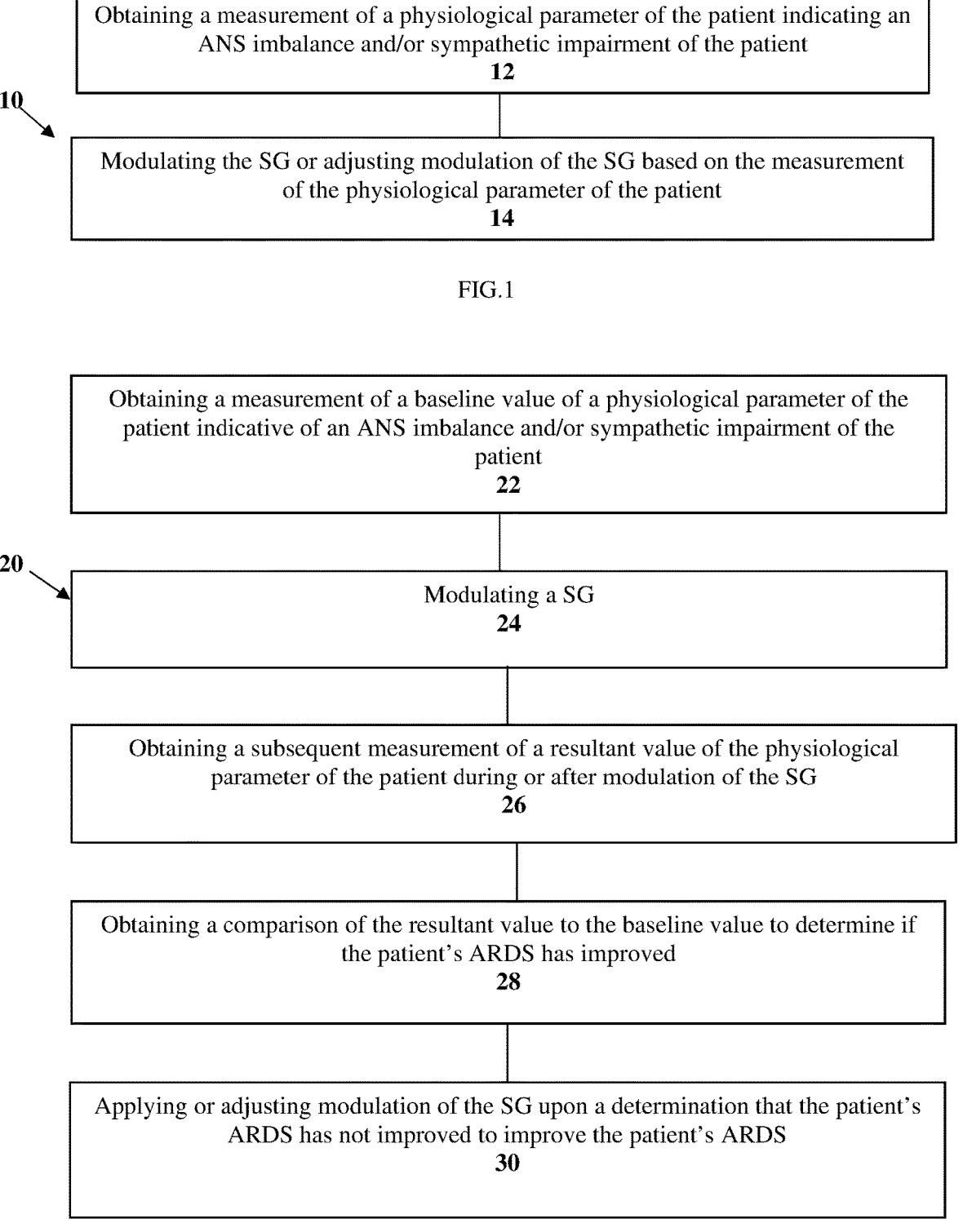
FIG. 1 is flow diagram of exemplary steps of a method according to an aspect of the present disclosure.
FIG. 2 is a flow diagram of exemplary steps of a method according to an aspect of the present disclosure.

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. By "improving" a condition, the patient's condition is less severe after therapy than before therapy. A "patient" as used herein includes a mammal, such as a human being.

Methods, systems and devices are provided herein to improve ANS imbalance and/or sympathetic impairment mediated by the stellate ganglion and other components of the sympathetic nervous system/parasympathetic nervous system in a patient in need thereof. Such ANS imbalance and/or sympathetic impairment can include ANS dysregulation (tone), sympathetic imbalance or sympathetic/parasympathetic imbalance, sympathetic irritability, sympathetic irregularity, abnormal frequency changes or patterns of neural electrical activity, sympathetic hypoactivity, or sympathetic hyperactivity. For example, ANS imbalance and/or sympathetic impairment can include pulmonary and/or cardiac sympathetic hyperactivity, reduced sympathetic tone activity, impaired sympathetic tone, irregular sympathetic tone, lack of sympathetic regulation, sympathetic imbalance, sympathetic homeostasis, sympathetic irritability, miscoordination with the parasympathetic nervous system or other manifestations of ANS imbalance and/or sympathetic impairment.

Improving patient's ANS imbalance and/or sympathetic impairment can include optimizing sympathetic and/or parasympathetic activity, normalizing imbalance between the sympathetic and parasympathetic activity, improving a dysregulated ANS state including a dysregulated sympathetic state, reducing a sensitized or hypersensitized ANS state including a sensitized or hypersensitized sympathetic state, reducing sympathetic irritability, improving sympathetic regulation, improving sympathetic adaptability, and combinations thereof.

In particular, improving the patient's ANS imbalance and/or sympathetic impairment can include, for example, slowing the progression of ARDS, improving recovery of lung function in ARDS, reducing cardiac arrhythmias associated with ARDS, reducing the utilization of extracorporeal machine oxygenation (ECMO), improving oxygenation to the patient's tissue, reducing multi-organ failure, or combinations thereof. Methods as provided herein can be used in conjunction with existing available medical treatment to reduce the morbidity, mortality, and aid in potential recovery from ARDS, including COVID-19 induced ARDS.

As referenced above, ARDS is acute pulmonary edema of non-cardiac origin with respiratory compromise and high mortality. ARDS can be a consequence of many conditions including sepsis, infection, trauma, post-operative status, pancreatitis, and intracranial pathology (e.g. neurogenic pulmonary edema). COVID-19 induced ARDS has a fulminant course and high mortality in the absence of any specific therapy against COVID-19. One of the early events in the evolution of ARDS is sympathetic imbalance, irritability, and/or surge/overactivity leading to the development of ARDS. In COVID-19 induced ARDS there can be a cytokine storm mediated mechanism, for example, through interleukins 2, 7, and 10, granulocyte colony stimulating factor, interferon-γ-inducible protein 10, monocyte chemoattractant protein 1, macrophage inflammatory protein 1 α, and tumor necrosis factor α. This sympathetic impairment can ultimately lead to an imbalance of ANS function and to ARDS.

The stellate ganglion (SG) is a sympathetic ganglion located in the lower neck on either side and is made up of the fusion of the inferior cervical ganglion and the first thoracic ganglion. In a minority of individuals, the inferior cervical ganglion itself acts as the stellate ganglion (a normal anatomical variation). The SG is an important anatomical sympathetic gateway/node to the heart and lung with afferent and efferent inputs. Sympathetic inputs and outputs from the lung and heart are impacted by the stellate and as a result the stellate ganglion is an important anatomical node for intervention of neural inputs and outputs associated with the lung and heart. ARDS is associated with ANS imbalance and/or sympathetic impairment, such as, for example, a hyper sympathetic response, with local activation and priming of the SG and input to the brain and output to the heart and the lungs.

Without being bound to a particular mechanism of action, regulating the SG by blocking, normalizing, reducing, increasing, or otherwise effectively modulating afferent and efferent pathways to the heart and lung can improve function and disease, such as kidney function, cardiac function, cardiopulmonary function, neural function, ocular function, nasal function, liver function, lung and other pulmonary function, blood vessel function, heart function, gastrointestinal function, immune function, endocrine function or combinations thereof. For example, regulating the SG can affect the pulmonary afferent fibers routed through the SG to the dorsal root ganglion (DRG) to the spinal cord and to brain and can also block the sympathetic efferent fibers that results in increased pulmonary sympathetic tone. As such, a sympathetic ganglion block (SGB) or other form of regulating the SG can modulate and improve the function of the lung and the heart; improve recovery of lung function in ARDS such as, for example, reducing blood clots in the patient's lungs; improve overall function of the lung in ARDS; improve overall cardiac function such as, for example, decrease the incidence of arrhythmias, improve heart failure, cardiomyopathy, and/or heart contractility associated with ARDS; improve vascular state such as, for example, reduce the constriction of blood vessels leading to and from the lungs; reduce the utilization of ECMO for ARDS; reduce the need for ventilators and intubation; improve impaired sympathetic input and output from the heart and the lung; or combinations thereof.

Other associated non-limiting effects of modulating or regulating the SG, such as by administering an SGB, can include stopping or reducing cardiac arrhythmias that accompany the sympathetic impairment associated with ARDS; providing organ specific sympathetic neuromodulation of lung tissue; arresting the progress of ARDS or even reversing it; reducing, normalizing or optimizing local sympathetic tone in pulmonary vasculature and the pulmonary system; reducing the abnormal inflammatory response in lung tissue; correcting associated cardiac functional issues; improving pulmonary outcome measures such as PaO2/FiO2 ratio, improving imaging and clinical outcome, biomarker outcomes of ARDS; or combinations thereof.

In an aspect, a method of improving ANS imbalance and/or sympathetic impairment in a patient suffering therefrom comprises administering a SGB to the patient or otherwise modulating or regulating the SG to improve the patient's ANS imbalance and/or sympathetic impairment. The ANS imbalance and/or sympathetic impairment can manifest as ARDS including COVID-19 induced ARDS. Improving ANS imbalance and/or sympathetic impairment can include, for example, improving the patient's lung function; improving the patient's cardio-pulmonary sympathetic hyperactivity including reducing cardiac arrythmias; reducing the utilization of ECMO; improving sympathetic tone; or combinations thereof.

The SG can be modulated or otherwise regulated in different ways. For example, an SGB can be administered to the SG (including adjacent to the SG such that a SGB can be achieved or the SG is otherwise modulated or regulated). For example, a SGB can be administered by delivering a therapeutically effective dose of a chemical substance to the patient's SG. The chemical substance can be a liquid, a gel, a sustained release polymer such as PLA and others, for example. The chemical substance can be encased in a capsule, can be a pellet, sphere or have other shapes and formulations for delivery. The chemical substance can be, for example, an anesthetic, an opioid, a steroid, a toxin, an agonist of neuronal receptors and/or synaptic function, an antagonist of neuronal receptors or synaptic function, other medications, or suitable combinations thereof.

Non-limiting examples of an anesthetic include bupivacaine, lidocaine, or combinations thereof. A non-limiting example of a steroid includes dexamethasone. Non-limiting examples of a toxin including a botulinum toxin, including, for example, botulinum toxin type A, B, C1, D, E, F or G. Non-limiting examples of other medications include analgesics, anorexiants, anticonvulsants, antiemetic/antivertigo agents, anti-Parkinson agents, anxiolytics, sedatives, hypnotics, cholinergic agonists, cholinesterase inhibitors, CNS stimulants, drugs used in alcohol or other forms of drug dependence, general anesthetics, miscellaneous central nervous system agents, muscle relaxants, VMAT2 inhibitors, or suitable combinations thereof.

Non-limiting examples of analgesics include analgesic combinations, antimigraine agents, CGRP inhibitors, cox-2 inhibitors, miscellaneous analgesics, narcotic analgesic combinations, narcotic analgesics, non-steroidal anti-inflammatory drugs, salicylates, or suitable combinations thereof. Non-limiting examples of anticonvulsants include AMPA receptor antagonists, barbiturate anticonvulsants, benzodiazepine anticonvulsants, carbamate anticonvulsants, carbonic anhydrase inhibitor anticonvulsants, dibenzazepine anticonvulsants, fatty acid derivative anticonvulsants, gamma-aminobutyric acid analogs, gamma-aminobutyric acid reuptake inhibitors, hydantoin anticonvulsants, miscellaneous anticonvulsants, neuronal potassium channel openers, oxazolidinedione anticonvulsants, pyrrolidine anticonvulsants, succinimide anticonvulsants, triazine anticonvulsants, or suitable combinations thereof. Non-limiting examples of antiemetic/antivertigo agents includ5HT3 receptor antagonists, anticholinergic antiemetics, miscellaneous antiemetics, NK1 receptor antagonists, phenothiazine antiemetics, or suitable combinations thereof. Non-limiting examples of anti-Parkinson agents include anticholinergic anti-Parkinson agents, dopaminergic anti-Parkinsonism agents, miscellaneous anti-Parkinson agents, and suitable combinations thereof. Non-limiting examples of anxiolytics, sedatives, and hypnotics include barbiturates, benzodiazepines, miscellaneous anxiolytics, sedatives and hypnotics, and suitable combinations thereof. Non-limiting examples of muscle relaxants include neuromuscular blocking agents, skeletal muscle relaxant combinations, skeletal muscle relaxants, and suitable combinations thereof.

Other methods of modulating or otherwise regulating the SG include performing a surgical sympathectomy of the patient's SG; performing radiofrequency lesioning of the patient's SG; delivering optical irradiation, such as linear polarized light irradiation, to the patient's SG, delivering ultrasound energy, such as focused ultrasound, to the patient's SG; delivering electrical neurostimulation to the patient's SG; or suitable combinations thereof including deliver of other forms of electromagnetic energy including acoustic, magnetic, optical, infrared, or suitable combinations thereof. The SG can be modulated unilaterally or bilaterally. For example, the SGB can be administered unilaterally or bilaterally to the patient's SG. The delivery of an SGB can be done continuously (e.g. continuous infusion of a chemical substance) or intermittently and can be done in a manner to provide targeted delivery.

An SGB can also be administered with ultrasound-guided imaging. For example, a needle or other therapy delivery device can include or be used in conjunction with an ultrasound probe to localize the SG in the patient. For instance, a method for guiding a therapy delivery device to the SG can include using ultrasound imaging to obtain an ultrasound image of anatomical structures relevant to the SG target and determining a delivery pathway based on the ultrasound image. The delivery pathway can define a trajectory that avoids the relevant anatomical structures and extends between an insertion point on the skin of the subject and the SG. The method can further include inserting a needle or other therapy delivery device into the insertion point, navigating the therapy delivery device through the delivery pathway until the distal tip is positioned adjacent or proximate to the SG and then delivering the therapy. The steps can be performed using real-time ultrasound imaging.

Ultrasound can also be used in a therapeutic manner. For example, focused ultrasound can be delivered via a needle or an external non-invasive source to provide targeted modulation of the SG.

In certain aspects, methods as disclosed herein include feedback mechanisms (including open or closed-loop feedback mechanisms) to adjust or apply therapy. Referring to FIG. 1, in an aspect, a method 10 of improving ANS imbalance and/or sympathetic impairment in a patient suffering therefrom (including such an imbalance or impairment manifested as ARDS) comprises obtaining a measurement of a physiological parameter of the patient 12 and modulating the SG or adjusting modulation of the SG based on the measurement of the physiological parameter of the patient 14. For example, modulating the SG based on the measurement of the physiological parameter can include administering a SGB or adjusting administration of a SGB. Referring to FIG. 2, in an aspect, a method 20 of improving ANS imbalance and/or sympathetic impairment in a patient suffering therefrom (including such an imbalance or impairment manifested as ARDS) comprises obtaining a measurement of a baseline value of a physiological parameter of the patient 22, modulating a SG 24, obtaining a subsequent measurement of a resultant value of the physiological parameter of the patient during or after modulation of the SG 26, obtaining a comparison of the resultant value to the baseline value to determine if the patient's autonomic nervous system imbalance and/or sympathetic impairment has improved 28, and applying or adjusting modulating of the SG upon a determination that the patient's ANS imbalance and/or sympathetic impairment has not improved to improve the patient's ANS imbalance and/or sympathetic impairment 30. For example, with respect to a SGB, a method of improving imbalance of ANS function and/or sympathetic impairment in a patient suffering therefrom can comprise obtaining a measurement of a baseline value of a physiological parameter of the patient, administering a SGB, obtaining a subsequent measurement of a resultant value of the physiological parameter of the patient during or after administration of the SGB, obtaining a comparison of the resultant value to the baseline value to determine if the patient's ANS imbalance and/or sympathetic impairment has improved, and applying or adjusting administration of one or more subsequent SGBs upon a determination that the patient's ANS imbalance and/or sympathetic impairment has not improved to improve the patient's ANS imbalance and/or sympathetic impairment.

The physiological parameter can be any suitable physiological parameter, for example, that provides an indication of the patient's ANS state and/or sympathetic state, such as the presence, absence, and/or degree of ANS imbalance and/or sympathetic impairment. For example, the physiological parameter can be a component of bodily fluid, a radiographic or other internal image of the patient's body, cardiac or cardiovascular function, lung or respiratory function, neural activity, including chemical and electrical activity of the SG and/or its tributaries, or combinations thereof. Non-limiting examples of components of bodily fluids include blood biomarkers such as levels of coagulation parameters such as d-dimer; ferritin; troponin (including troponin T or I); lactase dehydrogenase (LDH); certain cytokine profiles; basic metabolic panel (BMP); blood counts; or combinations thereof. For example, increases in d-dimer levels (e.g. ≥1 µg/mL), ferritin and Interlukin-6 can indicate that the patient is in need of a SGB or other parameters of the SGB need to be adjusted for the therapy to be sufficiently efficacious to improve the patient's condition (e.g. dose, duration, intervals between administration if multiple administrations are provided). Similarly, decreases in PaO2/FiO2 levels can also indicate that the patient is in need of a SGB or other parameters of the SGB need to be adjusted for the therapy to be sufficiently efficacious to improve the patient's condition. Other biomarkers include urine metabolites and microbiological and virological assessment data.

Regarding cytokine profiles, a cytokine profile resembling secondary hemophagocytic lymphohistiocytosis (sHLH) can be associated with COVID-19 disease severity, characterized by increased Interleukin IL-2, IL-7, Granulocyte colony stimulating factor, Interferon-γ inducible protein 10, Monocyte chemoattractant protein 1, Macrophage inflammatory protein 1-α, and Tumour necrosis factor-α. Secondary hemophagocytic lymphohistiocytosis (sHLH) is a hyperinflammatory syndrome characterized by fulminant and fatal hypercytokinaemia, multiorgan failure, or combinations thereof. In adults, sHLH is most commonly triggered by viral infections and in minority with sepsis (3.7-4.3%). Features of sHLH include unremitting fever, cytopenias, hyperferritinaemia and pulmonary involvement (including ARDS).

Non-limiting examples of radiographic or other internal imaging include chest x-rays, CT scans, and combinations thereof. Non-limiting examples of cardiac or cardiovascular function that can be used to provide feedback to the therapy include heart rate (HR); heart rate variability; pulmonary wedge pressure (PWP); pulmonary vascular resistance (PVR); systolic (SAP), diastolic (DAP), and mean (MAP) arterial pressures; left-ventricular hemodynamic and/or mechanical/geometrical indices obtained from the pressure signal (ESP, EDP, dP/dtmax/min, time-constant of relaxation (tau), contractility-index—Vmax); cardiac output; mean right-atrial (RAP) and pulmonary-artery (PAP) pressures; estimated systemic/pulmonary vascular resistance (SVR/PVR), Chest x-ray, cardiac arrhythmia, and combinations thereof. Non-limiting examples of lung or respiratory function that can be used to provide feedback to the therapy include the patient's PaO2/FiO2 ratio (compared to a baseline value, for example), respiratory rate, intratracheal pressure (ITP), and chest X-ray. For example, if the patient's PaO2/FiO2 ratio is ≤150 mm Hg, then this can indicate that the patient is in need of a SGB or other parameters of the SGB need to be adjusted for the therapy to be sufficiently efficacious to improve the patient's condition.

Other physiological parameters that can be monitored to provide feedback to therapy include sleep, sleep stage, and skin temperature. Non-invasive modalities using wearable technology can measure changes in respiratory rate, skin temperature, heart rate, heart rate variability, galvanic skin response, and other measures of sympathetic and/or parasympathetic nervous system activity, for example. Wearable devices, such as a ring, can continuously monitors different metrics during sleep (e.g. heart rate, heart rate variability, respiratory rate, skin temperature) and sleep quality measurements such as sleep stage tracking. Such a device can connect to a smartphone phone, for example, via Bluetooth where data can be accessed by the user or their care provider.

Regarding recording electrical activity from the SG or other nerves that receive input/output from the SG, such activity can be recorded from the electrode that is used to deliver electrical stimulation to the SG in embodiments where electrical stimulation is the mode of treatment or from another electrode of an electrical stimulation system used for treatment. The electrode can be, for example, a percutaneous needle inserted in the neck to record electrical activity of the SG of nerves that receive input or output from the SG. Alternatively, the electrode can be a recording electrode external to the patient's body. Such recorded electrical activity can be used as feedback to provide an indication of the patient's ANS state and/or sympathetic state, such as the presence, absence, and/or degree of ANS imbalance and/or sympathetic impairment. Alternatively or in addition, chemical activity of the SG or other nerves that receive input/output from the SG can be recorded from biosensors.

The assessment of physiological parameters can be performed directly or indirectly and can be performed external to the body via a wearable device for example or a device otherwise removed from the body, percutaneously, within the body with an implantable device, for example, or combinations thereof.

Feedback mechanisms can be also be used to determine how to improve the patient's tissue oxygenation; improve the patient's vascular tone, improve the patient's vital signs; determine/adjust ventilator settings such as, for example, FiO2, SpO2, PEEP, and oxygen saturation; improve the patient's laboratory values such as, for example, d-dimer, ferritin, troponin, CRP, and other inflammatory factors. Feedback mechanisms can also be used to treat shock (septic and others) secondary to ARDS. Feedback mechanisms can also be used to adjust other therapies used for ARDS such as nitric oxide, decadron, heparin, remdesivir, and other treatments for ARDS.

Improving the patient's ARDS can include improving acute as well as chronic effects of ARDS. For example, improving the patient's ARDS can include improving chronic cardiovascular effects, including chronic heart failure for example, and/or pulmonary effects, including for example, a patient's pulmonary vascular disease.

Improving chronic effects of ARDS can be important since as a patient recovers from acute ARDS, there can be lingering long term effects impacting various bodily system functions.

Improving the patient's ARDS can also include, as mentioned above, improving the patient's pulmonary and systemic vascular compromise and hypercoagulability. Many patients with ARDS, such as COVID-19 can be markedly hypoxemic but are not in need of a ventilator. COVID-19 may directly impact oxygen loading and transport by hemoglobin. Also, patients suffering from ARDS, such as COVID-19, have shown of widespread vascular thrombosis and a Disseminated intravascular coagulation (DIC)-like picture resulting in ischemic limb injury, heart failure and dialysis-dependent renal failure, even if they recover. Cytokine induction and immune hyperactivity seems part of this pathogenesis, as well. The hypersympathetic tone induced through the SG may drive this sympathetic vascular dysfunction that may secondarily cause hypercoaguability and unregulated clotting. While ARDS, such as COVID-19 appear to primarily impact the pulmonary and cardiac systems, the critical role of this cardiopulmonary axis in regulating vascular homeostasis means that regulating the SG to reduce disease severity and enhance recovery by improving system vascular disease and hypercoaguability can be an important treatment factor. A hypersympathetic vascular state that induces vasoconstriction and augments coaguability of blood, platelets and clotting factors could be at the root of the pathogenesis of mutli-organ compromise in patients dying of COVID-19. Regulating the SG, such as through an SGB, may serve to reset this hyper-sympathetic tone and improve not only respiratory failure.

Physiological parameters or conditions that could be monitored to determine the presence of such vascular compromise include thrombocytosis or thrombocytopenia, CRP/IL6 elevation, evidence of DIC in blood screen, and right heart strain, for example. Therapy could be modified as result of such monitored physiological parameters. For example, therapy approaches could include anti-inflammatory treatment, prostacyclin/VIAGRA administration, heparin administration, fluid treatment (treatment similar to treating obstructive shock as opposed to sepsis for example).

In certain aspects, the patient can suffer from one or more of hypertension, diabetes, or coronary heart disease. Mortality in COVID-19 may be due to virally driven hyper-inflammation. A subgroup of patients with severe COVID-19 may have a cytokine storm syndrome and methodologies as disclosed herein may be used on such patient populations.

In another aspect, a method of improving a patient suffering from a hypercoagulability state is provided. Such a hypercoagulable state can be the result of homeostatic imbalance such as sympathetic hyperactivity. Such a hypercoagulable state can be caused by infection, trauma or other insult. Such a hypercoagulable state can cause multi-organ disease and/or failure such as kidney disease, limb amputation, and/or ischemia or damage of end organs such as the skin, gastrointestinal system, liver, spleen, kidney and combinations thereof. Such a method includes regulating the patient's autonomic nervous system, such as the sympathetic nervous system to improve the patient's hypercoagulability state. Non-limiting examples of autonomic system target sites to improve a hypercoagulability state include autonomic nerves (including pre- and post-ganglionic fibers of the ANS), autonomic ganglia, and autonomic plexus. Preferably, the neural target site is a part of the SNS, such as a sympathetic ganglion, a sympathetic nerve or a sympathetic plexus. Regarding sympathetic ganglia, the neural target site can be a prevertebral ganglion or a paravertebral ganglion (sympathetic nerve chain ganglion) or the sympathetic trunk. Examples of paravertebral ganglia include a cervical ganglion, a thoracic ganglion, a lumbar ganglion, and a sacral ganglion. Cervical ganglia include a superior cervical ganglion, a middle cervical ganglion, and an inferior cervical ganglion (or a stellate ganglion). Examples of prevertebral ganglia include a celiac ganglion, an aorticorenal ganglion, a superior mesenteric ganglion, and an inferior mesenteric ganglion. Regarding sympathetic nerves, the neural target site can be a splanchnic nerve, including a greater, lesser, and least splanchnic nerve. Regarding autonomic plexus, the neural target site can be a superior hypogastric plexus or a pulmonary plexus. The target site can also be another site of the peripheral nervous system such as, for example, a spinal nerve, a spinal ganglion, a spinal plexus or a localized intrinsic nervous system of an organ. For example, the neural target site can be a dorsal root ganglion, a lumbar plexus, or a hypogastric nerve. Feedback mechanism can also be used to adjust/apply treatment using physiological parameters/conditions as described above relating to a patient's vascular state.

EXAMPLE

The SG is located with the standard clinical landmark in relation with Chassaignac's tubercle on the C6 transverse process or acceptable practicing procedural variation per the physician. Anatomical landmarks and/or fluoroscopy/ultrasound guidance is used to locate and place the needle. Once location is confirmed, up to 5-10 milliliters of a local anesthetic such as lidocaine 1-2% or 0.25% bupivacaine with 4 mg Dexamethasone is injected next to the SG.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:

1. A method of improving acute respiratory distress syndrome (ARDS) in a human patient suffering therefrom comprising:
   delivering a therapeutically effective dose of an anesthetic to the human patient's stellate ganglion (SG) to regulate function of the SG to improve the human patient's ARDS wherein the anesthetic is selected from lidocaine, bupivacaine or combinations thereof.

2. The method of claim 1, wherein improving the patient's ARDS comprises improving autonomic nervous system (ANS) imbalance and/or sympathetic impairment in the patient.

3. The method of claim 1, wherein improving the patient's ARDS comprises improving the patient's, cardiac function, cardiopulmonary function, neural function, ocular function, nasal function, liver function, blood vessel function, heart function, pulmonary function, immune function, endocrine function, kidney function, gastrointestinal function, or combinations thereof.

4. The method of claim 1, wherein improving the patient's ARDS comprises improving the cardio-pulmonary sympathetic hyperactivity, sympathetic sensitization, sympathetic dysregulation, or combinations thereof in the patient.

5. The method of claim 1, wherein the patient suffers from COVID-19 induced ARDS and improving the patient's ARDS comprises improving the patient's COVID-19 induced ARDS.

6. The method of claim 1, wherein improving the patient's ARDS comprise improving the patient's lung function.

7. The method of claim 1, wherein improving the patient's ARDS comprises improving the patient's heart failure, reducing the patient's cardiac arrythmias, improving the patient's cardiomyopathy, improving the patient's heart contractility, or combinations thereof.

8. The method of claim 1, wherein improving the patient's ARDS comprises reducing the utilization of extra-corporeal membrane oxygenation (ECMO), improving ventilator settings, reducing cardiopulmonary support interventions, or combinations thereof.

9. The method of claim 1, wherein improving the patient's ARDS comprises improving the patient's sympathetic tone, sympathetic activity, sympathetic/parasympathetic balance, sympathetic irritability, sympathetic sensitization, sympathetic regulation, or combinations thereof.

10. The method of claim 9, wherein improving the patient's sympathetic tone facilitates function and homeostasis and improves the patient's disease or function.

11. The method of claim 1, wherein improving the patient's ARDS comprises reducing blood clots and hyper-coagulation in the patient's cardiopulmonary and peripheral vascular system.

12. The method of claim 1, wherein improving the patient's ARDS comprises improving the patient's vascular status.

13. The method of claim 12, wherein improving the patient's ARDS comprises reducing constriction of blood vessels leading to and from the patient's lungs.

14. The method of claim 1, wherein improving the patient's ARDS comprises acutely improving the patient's ARDS, improving chronic effects of ARDS, and combinations thereof.

15. A method of improving ARDS in a patient suffering therefrom comprising the steps of:
   obtaining a measurement of a physiological parameter of the patient indicative of ANS imbalance and/or sympathetic impairment; and
   delivering a therapeutically effective dose of an anesthetic to the patient's stellate ganglion (SG) to regulate and optimize the function of the SG based on the measurement of the physiological parameter of the patient to improve the patient's ARDS wherein the anesthetic is selected from lidocaine, bupivacaine or combinations thereof.

16. A method of improving ARDS in a patient suffering therefrom comprising:
   obtaining a measurement of a baseline value of a physiological parameter of the patient indicative of ANS imbalance, sympathetic sensitization, sympathetic dysregulation and/or sympathetic impairment;
   delivering a therapeutically effective dose of an anesthetic to the patient's stellate ganglion (SG) to regulate function of the SG;
   obtaining a subsequent measurement of a resultant value of the physiological parameter of the patient during or after delivering the therapeutically effective dose of the anesthetic to the SG;
   obtaining a comparison of the resultant value to the baseline value to determine if the patient's ARDS has improved; and applying or adjusting delivery of the therapeutically effective dose of the anesthetic to the SG based upon a determination that the patient's ARDS has not improved to improve the patient's ARDS wherein the anesthetic is selected from lidocaine, bupivacaine or combinations thereof.

17. The method of claim 1, wherein the anesthetic is lidocaine.

18. The method of claim 15, wherein the anesthetic is lidocaine.

19. The method of claim 16, wherein the anesthetic is lidocaine.

* * * * *